US00PP31554P2

(12) United States Plant Patent
van den Hoogen

(10) Patent No.: US PP31,554 P2
(45) Date of Patent: Mar. 17, 2020

(54) ***VERONICA* PLANT NAMED 'ALLFOUNT'**

(50) Latin Name: ***Veronica longifolia* x *Veronica Spicata***
Varietal Denomination: Allfount

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 16/350,173

(22) Filed: Oct. 10, 2018

(51) Int. Cl.
*A01H 5/02* (2018.01)
*A01H 6/00* (2018.01)

(52) U.S. Cl.
USPC ..... Plt./251

(58) Field of Classification Search
USPC ..... Plt./251
See application file for complete search history.

(56) References Cited

PUBLICATIONS

UPOV-PLUTO: Plant Variety Database—(Jun. 21, 2019) denomination for 'ALLFOUNT' (1 page).*
www.hortipoint.nl/floribusiness/ereprijs-speciaal-2/ (retrieved on Jun. 24, 2019 from the Internet) (4 pages total).*

* cited by examiner

*Primary Examiner* — Susan McCormick Ewoldt
(74) *Attorney, Agent, or Firm* — C. A. Whealy

(57) ABSTRACT

A new and distinct cultivar of *Veronica* plant named 'Allfount', characterized by its upright plant habit; dark green-colored leaves; freely flowering habit; dense inflorescences with numerous violet-colored flowers; and good performance as a garden plant and as a cut flower.

2 Drawing Sheets

Botanical designation: *Veronica longifolia* x *Veronica spicata.*
Cultivar denomination: 'ALLFOUNT'.

BACKGROUND OF THE INVENTION

The present invention relates to a new and distinct cultivar of *Veronica* plant, botanically known as *Veronica longifolia* x *Veronica spicata*, typically grown as a cut flower and hereinafter referred to by the name 'Allfount'.

The new *Veronica* plant is a product of a planned breeding program conducted by the Inventor in Cuijk, The Netherlands. The objective of the breeding program is to create new attractive *Veronica* plants with unique inflorescence form.

The new *Veronica* plant originated from an open-pollination in August, 2013 of a proprietary selection of *Veronica longifolia* x *Veronica spicata* identified as code number 1-2013-80, not patented, as the female, or seed, parent with an unknown selection of *Veronica longifolia* x *Veronica spicata* as the male, or pollen, parent. The new *Veronica* plant was discovered and selected by the Inventor as a single flowering plant from within the progeny of the stated open-pollination in a controlled nursery environment in Cuijk, The Netherlands in June, 2014.

Asexual reproduction of the new *Veronica* plant by terminal cuttings in a controlled environment in Cuijk, The Netherlands, since September, 2014 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allfount'. These characteristics in combination distinguish 'Allfount' as a new and distinct *Veronica* plant:

1. Upright plant habit.
2. Dark green-colored leaves.
3. Freely flowering habit.
4. Dense inflorescences with numerous violet-colored flowers.
5. Good performance as a garden plant and as a cut flower.

Plants of the new *Veronica* differ primarily from plants of the female parent selection in the following characteristics:

1. Inflorescences of plants of the new *Veronica* are compound racemes whereas inflorescences of plants of the female parent selection are a single spike with secondary smaller spikes.
2. Flowers of plants of the new *Veronica* are violet in color whereas flowers of plants of the female parent selection are pink in color.

Plants of the new *Veronica* can be compared to plants of *Veronica longifolia* x *Veronica spicata* 'Alllaguna', disclosed in U.S. Plant Pat. No. 27,506. In side-by-side comparisons, plants of the new *Veronica* differ primarily from plants of 'Alllaguna' in the following characteristics:

1. Inflorescences of plants of the new *Veronica* are compound racemes whereas inflorescences of plants of 'Alllaguna' are fasciated racemes.

2. Flowers of plants of the new *Veronica* are violet in color whereas flowers of plants of 'Alllaguna' are dark blue in color.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Allfount' grown in a container.

The photograph on the second sheet is a close-up view of a typical inflorescence of 'Allfount'.

DETAILED BOTANICAL DESCRIPTION

Plants used for the aforementioned photographs and following description were grown during the spring in an outdoor nursery in Kenya and under cultural practices typical of commercial *Veronica* production. During the production of the plants, day temperatures ranged from 15° C. to 28° C. and night temperatures ranged from 5° C. to 15° C. Plants were one year old when the photographs and the description were taken. In the following description, color references are made to The Royal Horticultural Society Colour Chart, 2015 Edition, except where general terms of ordinary dictionary significance are used.

Botanical classification: *Veronica longifolia* x *Veronica spicata* 'Allfount'.

Parentage:

*Female, or seed, parent*.—Proprietary selection of *Veronica longifolia* x *Veronica spicata* identified as code number 1-2013-80, not patented.

*Male, or pollen, parent*.—Unknown selection of *Veronica longifolia* x *Veronica spicata*, not patented.

Propagation:

*Type cutting*.—Terminal cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial.

*Plant and growth habit*.—Upright plant habit; moderately vigorous growth habit and moderate growth rate.

*Plant height, soil level to top of foliar plane*.—About 60 cm.

*Plant height, soil level to top of floral plane*.—About 68 cm.

*Plant width*.—About 32.7 cm.

*Lateral branch description*.—Branching habit: Freely branching habit with about four main stems; pinching will enhance lateral branching. Length: About 62.8 cm. Diameter: About 4 mm. Internode length: About 4.8 cm. Strength: Strong. Aspect: About 30° from vertical. Texture and luster: Densely pubescent; slightly glossy. Color, developing: Close to 145B. Color, developed: Close to 144B.

Leaf description:

*Arrangement*.—Opposite, simple.

*Length*.—About 11.4 cm.

*Width*.—About 3 cm.

*Shape*.—Lanceolate; slightly curled downward, slightly to moderately carinate.

*Apex*.—Narrowly acute.

*Base*.—Truncate.

*Margin*.—Serrate.

*Texture and luster, upper surface*.—Sparsely pubescent; slightly rugose; moderately glossy.

*Texture and luster, lower surface*.—Sparsely pubescent; slightly rugose; matte.

*Venation pattern*.—Pinnate.

*Color*.—Developing leaves, upper surface: Close to 137A. Developing leaves, lower surface: Close to 147B. Fully expanded leaves, upper surface: Close to NN137A; venation, close to 152A. Fully expanded leaves, lower surface: Close to 147B; venation, close to 146C.

*Petioles*.—Length: About 1.4 cm. Diameter: About 2 mm. Strength: Strong. Texture and luster, upper surface: Densely pubescent; matte. Texture and luster, lower surface: Sparsely to moderately pubescent; moderately glossy. Color, upper surface: Close to 144A. Color, lower surface: Close to 144B.

Flower description:

*Flower arrangement and shape*.—Single campanulate flowers arranged on dense terminal compound racemes; flowers face mostly outwardly.

*Flowering habit*.—Freely flowering habit with about 2,000 flowers developing per inflorescence.

*Fragrance*.—None detected.

*Natural flowering season*.—Long flowering period; plants flower continuously from the spring until the autumn in The Netherlands.

*Flower longevity*.—Individual flowers last about 30 days on the plant and about 10 days as a cut flower; flowers persistent.

*Flower buds*.—Length: About 4.5 mm. Diameter: About 1.75 mm. Shape: Ovate to oblong. Texture and luster: Smooth, glabrous; matte. Color: Close to N88B; developing calyx, close to 138C.

*Inflorescence height*.—About 8.3 cm.

*Inflorescence diameter*.—About 8.2 cm.

*Flower diameter*.—About 5 mm by 6 mm.

*Flower height*.—About 7 mm.

*Petals*.—Quantity and arrangement: Four in a single whorl; petals fused about 40% of the petal length from the base. Length: About 5 mm. Width: About 2 mm to 3 mm. Shape: Oblong to broadly ovate; slightly concave. Apex: Obtuse. Margin: Entire. Texture and luster, upper surface: Distally, smooth, glabrous and proximally, densely pubescent; matte. Texture and luster, lower surface: Smooth, glabrous; matte. Color: When opening, upper and lower surfaces: Close to NN88B. Fully opened, upper and lower surfaces: Close to NN88A; color does not change with development.

*Sepals*.—Quantity and arrangement: Four arranged in a single whorl. Length: About 1 mm to 1.5 mm. Width: About 0.75 mm. Shape: Ovate. Apex: Acute. Base: Broadly cuneate, fused. Margin: Entire. Texture and luster, upper and lower surfaces: Smooth, glabrous; matte. Color: When opening, upper and lower surfaces: Close to 138C. Fully opened, upper and lower surfaces: Close to 137C.

*Peduncles*.—Length, terminal peduncle: About 4.8 cm. Length, axillary peduncle: About 6.3 cm. Diameter, terminal and axillary peduncles: About 3 mm. Aspect: Mostly upright. Strength: Strong. Texture and luster: Densely pubescent; slightly glossy. Color: Close to 144B.

*Pedicels*.—Length: About 1 mm. Diameter: About 0.5 mm. Aspect: About 50° from peduncle axis. Strength: Moderately strong. Texture and luster: Moderately pubescent; slightly glossy. Color: Close to 143C.

*Reproductive organs*.—Stamens: Quantity per flower: Typically two, occasionally one. Filament length: About 6 mm. Filament color: Close to N88A. Anther shape: Short oblong; dorsifixed. Anther size: About 1 mm by 0.5 mm. Anther color: Close to between N92A and 203C. Pollen amount: Moderate. Pollen color: Close to 4D. Pistils: Quantity per flower: One. Pistil length: About 7 mm. Stigma diameter: About 1 mm. Stigma shape: Club-shaped. Stigma color: Close to N144D. Style length: About 6 mm. Style color: Close to 86B; fading proximally to color to 86A. Ovary color: Close to 145A to 145B.

*Seeds and fruits*.—To date, seed and fruit development has not been observed on plants of the new *Veronica*.

Disease & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, high temperatures about 35° C. and to be suitable for USDA Hardiness Zones 4 through 9.

It is claimed:

1. A new and distinct *Veronica* plant named 'Allfount' as illustrated and described.

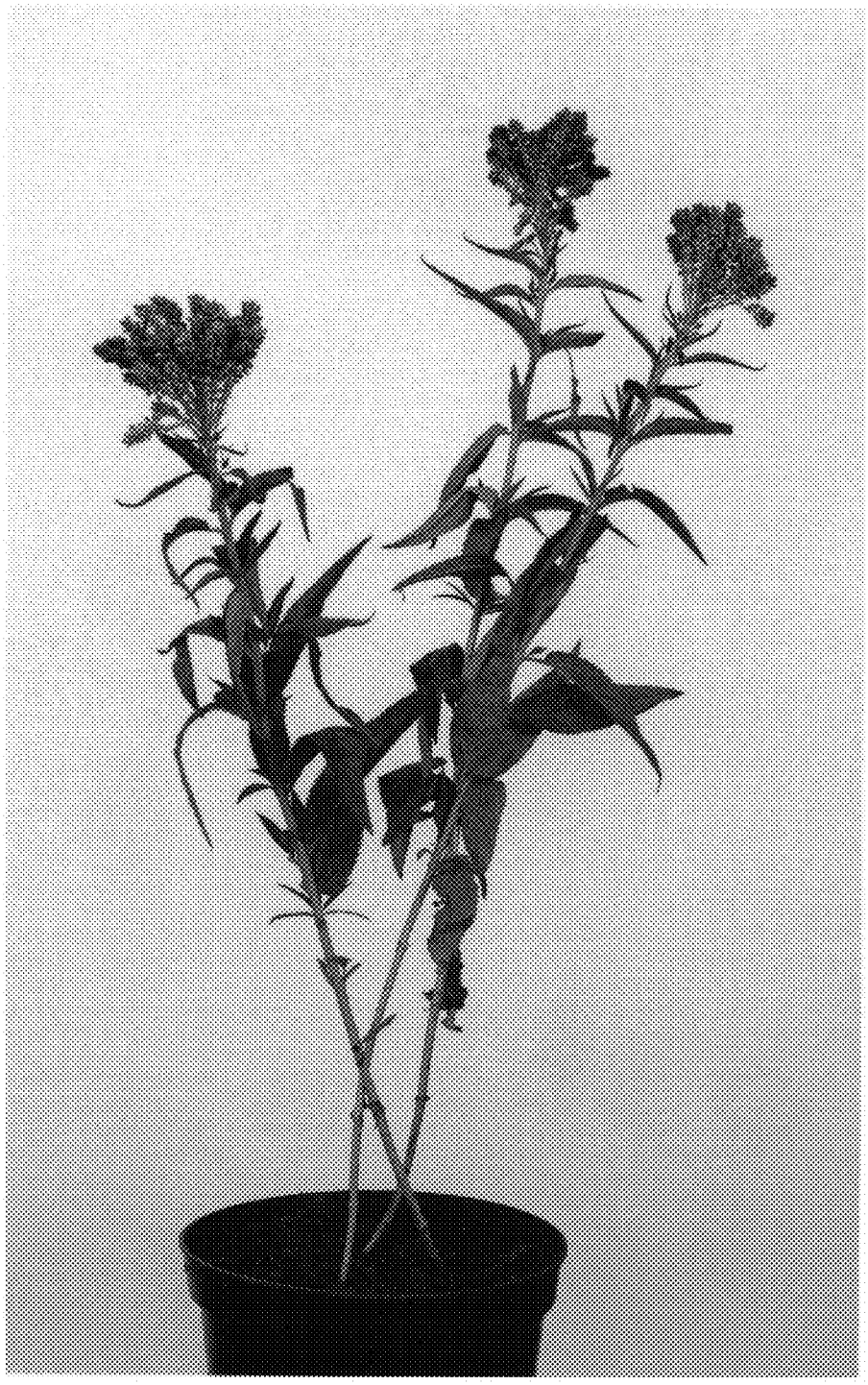

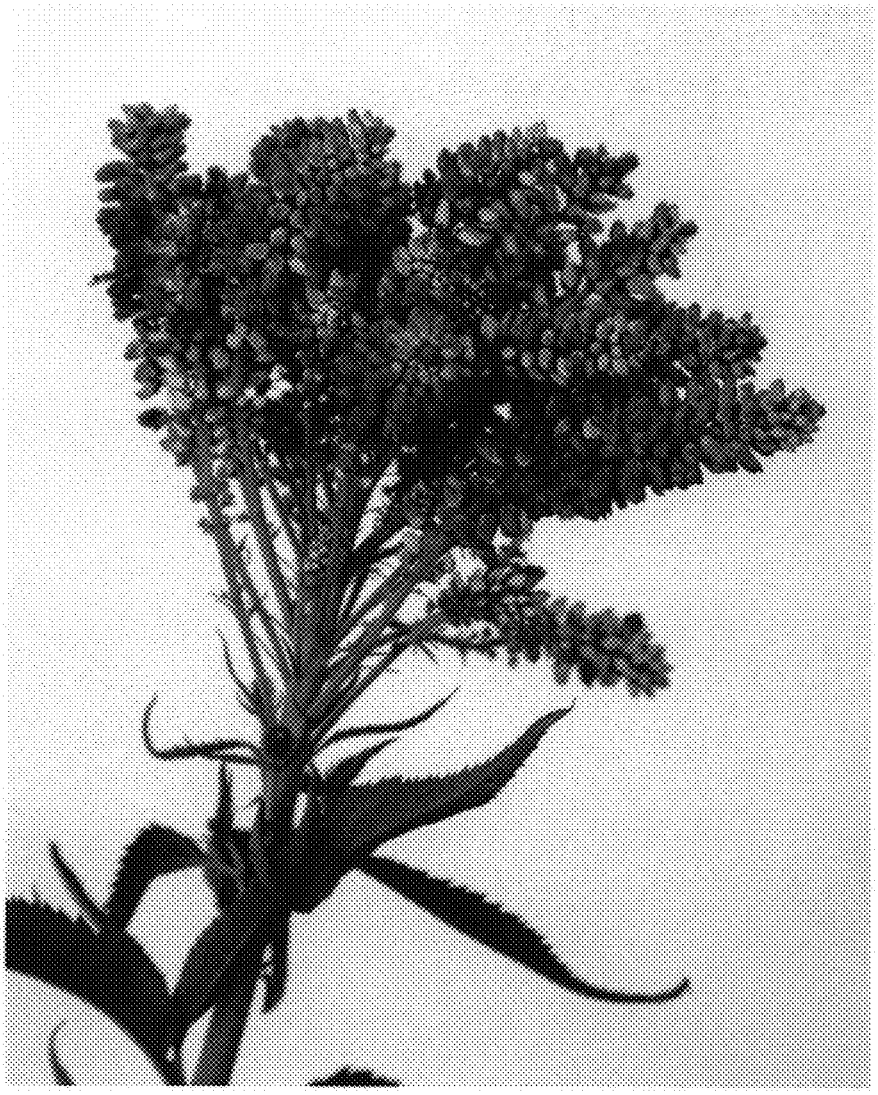
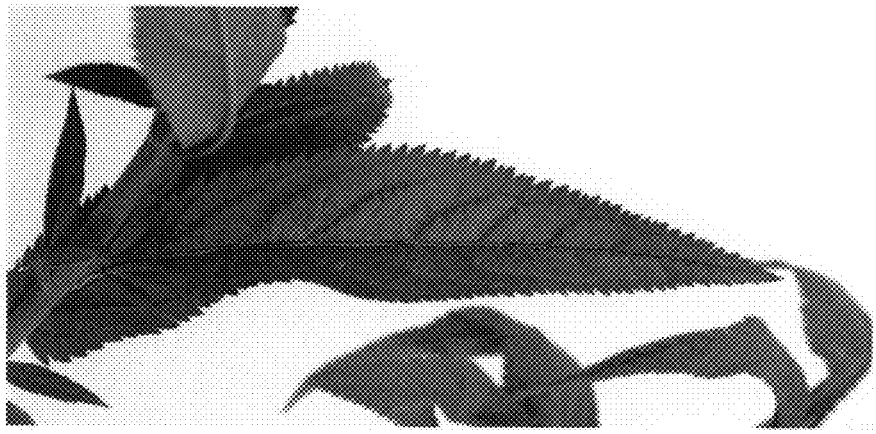

* * * * *